United States Patent
Czwaluk

(10) Patent No.: US 12,060,549 B2
(45) Date of Patent: Aug. 13, 2024

(54) METHOD FOR OPERATING A STIRRING DEVICE AND A FERMENTER

(71) Applicant: UTS BIOGASTECHNIK GMBH, Hallbergmoos (DE)

(72) Inventor: Andreas Czwaluk, Vechta (DE)

(73) Assignee: UTS BIOGASTECHNIK GMBH, Hallbergmoos (DE)

( * ) Notice: Subject to any disclaimer, the term of this patent is extended or adjusted under 35 U.S.C. 154(b) by 481 days.

(21) Appl. No.: 17/156,275

(22) Filed: Jan. 22, 2021

(65) Prior Publication Data

US 2021/0198610 A1 Jul. 1, 2021

Related U.S. Application Data

(63) Continuation of application No. 15/524,517, filed as application No. PCT/EP2015/075818 on Nov. 5, 2015, now Pat. No. 10,941,377.

(30) Foreign Application Priority Data

Nov. 7, 2014 (DE) .......................... 102014116239.0

(51) Int. Cl.
C12M 1/06 (2006.01)
B01F 27/25 (2022.01)
(Continued)

(52) U.S. Cl.
CPC ............. *C12M 27/02* (2013.01); *B01F 27/25* (2022.01); *B01F 27/704* (2022.01);
(Continued)

(58) Field of Classification Search
CPC ................... B01F 7/00733; B01F 15/00285; B01F 7/047; B01F 2215/0073; B01F 15/00389;
(Continued)

(56) References Cited

U.S. PATENT DOCUMENTS 8,818,562 B2 * 8/2014 Bluck .................... G05B 17/02
700/268
10,261,479 B2 * 4/2019 Krasberg ............. B01J 19/0033
(Continued)

FOREIGN PATENT DOCUMENTS

| CN | 102851408 A | 1/2013 |
| DE | 3920273 A1 | 1/1991 |
| DE | 10056338 A1 | 6/2001 |
| DE | 202007002835 U1 | 7/2007 |
| DE | 102010050863 A1 | 5/2012 |

(Continued)

OTHER PUBLICATIONS

International Preliminary Report on Patentability received for PCT/EP2015/075818 dated May 18, 2017.

*Primary Examiner* — Shogo Sasaki
(74) *Attorney, Agent, or Firm* — Greer, Burns & Crain, Ltd

(57) ABSTRACT

A method for operating an agitating device and a digester, wherein the digester is filled with a substrate and an agitating device is in the digester. These steps are performed: a) A target load curve is lodged in the control device; b) the control device prescribes a target rotation speed; c) the control device operates the agitating device at an actual speed corresponding to a target speed; d) the control device captures an actual agitating device torque measurement value at the actual speed of rotation; e) the control device derives from the actual measurement value an actual characteristic value of the agitating device applied torque; f) the control device compares the derived actual characteristic value against the target characteristic value of the substrate resulting from the target load curve at the prescribed target speed; and g) the control device controls the agitating device in dependence on the result of comparison.

15 Claims, 4 Drawing Sheets

(51) Int. Cl.

| | |
|---|---|
| *B01F 27/704* | (2022.01) |
| *B01F 27/705* | (2022.01) |
| *B01F 27/706* | (2022.01) |
| *B01F 33/81* | (2022.01) |
| *B01F 35/212* | (2022.01) |
| *B01F 35/22* | (2022.01) |
| *B01F 35/221* | (2022.01) |
| *C12M 1/107* | (2006.01) |
| *C12M 1/34* | (2006.01) |
| *C12M 1/36* | (2006.01) |
| *C12P 1/00* | (2006.01) |
| *B01F 101/44* | (2022.01) |

(52) U.S. Cl.
CPC .......... *B01F 27/705* (2022.01); *B01F 27/706* (2022.01); *B01F 33/81* (2022.01); *B01F 35/212* (2022.01); *B01F 35/2202* (2022.01); *B01F 35/221422* (2022.01); *C12M 21/04* (2013.01); *C12M 41/42* (2013.01); *C12M 41/48* (2013.01); *C12P 1/00* (2013.01); *B01F 2101/44* (2022.01); *Y02E 50/30* (2013.01)

(58) Field of Classification Search
CPC .......... B01F 15/00201; B01F 13/1013; C12M 21/04; C12M 27/02; C12M 41/42; C12M 41/48; C12P 1/00; Y02E 50/343
See application file for complete search history.

(56) References Cited

U.S. PATENT DOCUMENTS

| | | | |
|---|---|---|---|
| 2013/0029314 A1* | 1/2013 | Rostalski | ............... C12M 27/06 435/3 |
| 2013/0029315 A1* | 1/2013 | Rostalski | ............... C12M 27/06 435/3 |

FOREIGN PATENT DOCUMENTS

| | | |
|---|---|---|
| DE | 102012201609 A1 | 8/2013 |
| EP | 0516895 A1 | 12/1992 |
| EP | 1884561 A1 | 2/2008 |
| EP | 2559750 A1 | 2/2013 |
| EP | 2617483 A1 | 7/2013 |
| WO | 2011121022 A1 | 10/2011 |
| WO | 2011121024 A1 | 10/2011 |
| WO | 2014068016 A2 | 5/2014 |
| WO | 2016071447 A1 | 5/2016 |

* cited by examiner

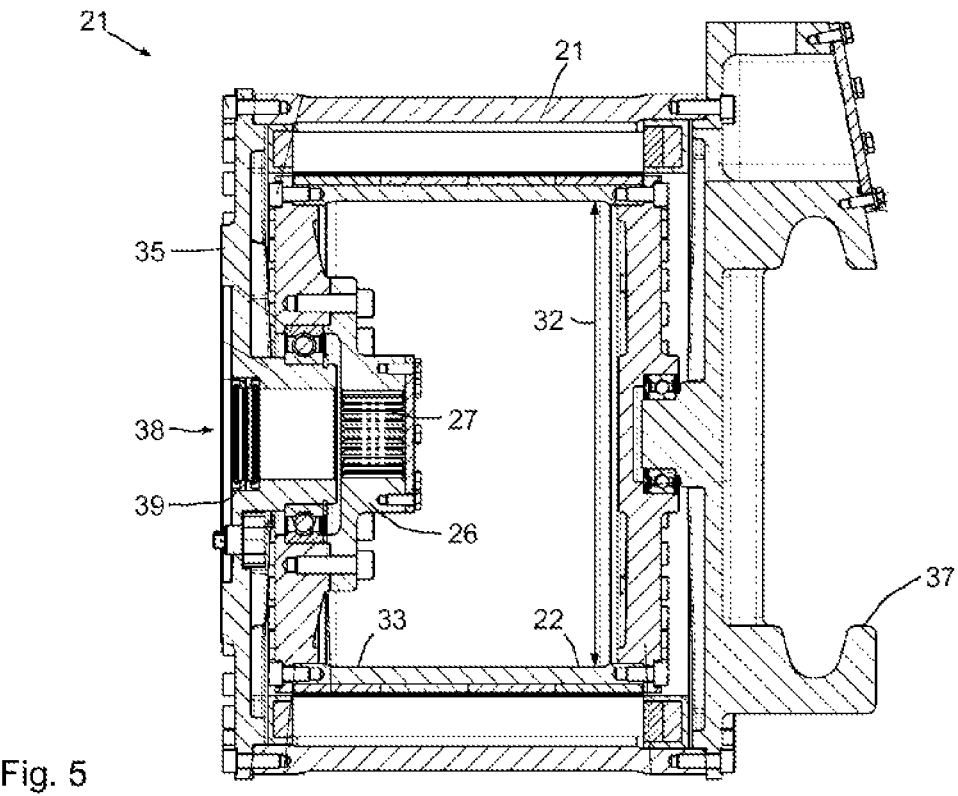
Fig. 5
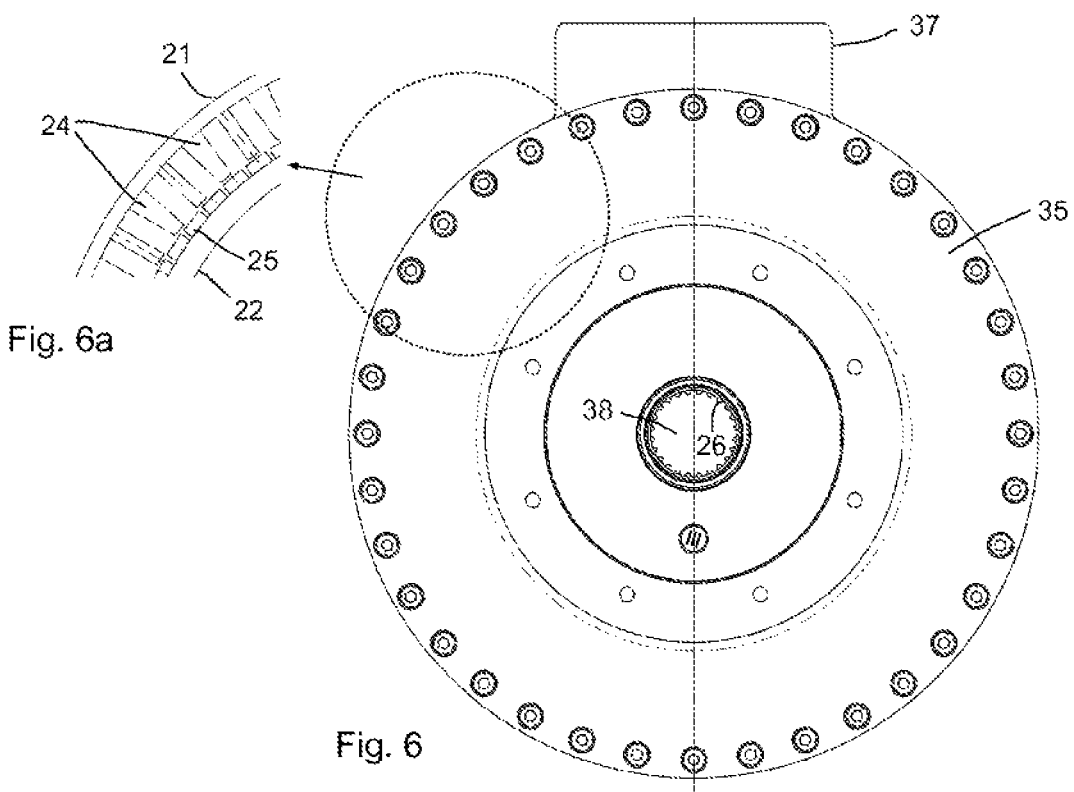
Fig. 6a
Fig. 6

METHOD FOR OPERATING A STIRRING DEVICE AND A FERMENTER

RELATED APPLICATIONS

This application is a continuation of, and claims priority under 35 U.S.C. 120 from Ser. No. 15/524,517, filed May 4, 2017, now U.S. Pat. No. 10,941,377 issued Mar. 9, 2021, which is a U.S. National Stage entry of International Application No. PCT/EP2015/075818, filed Nov. 5, 2015, which claims the benefit of German Application No. 102014116239.0, filed Nov. 7, 2014, all of which are incorporated by reference.

BACKGROUND

The present invention relates to a method for operating an agitating device and a digester for producing biogas comprising a digester at least partially filled with a substrate. At least one agitating device controlled by a control device is disposed in the digester.

The prior art has disclosed a number of methods for producing biogas which as a rule comprise at least one digester containing a substrate to which matter is added continuously or periodically. Above the substrate level, biogas accumulates which is removed, again continuously or periodically, for input into a gas supply network or else for generating power directly in the biogas plant.

WO 2011/121022 discloses a method and an apparatus for producing biogas from organic matter in which a tank is charged with a substrate by means of a feed system and where an agitator is provided in the tank for mixing the tank contents. By way of this known method the formation of cavities in the vicinity of the propellers is determined and a specific operational target value is specified in dependence thereon. The advantage of this method is that the formation of cavities in the vicinity of the propeller, i.e. immediately adjacent to the agitator blades, is taken into account. This regulation allows to reliably prevent cavitation. The drawback thereof is, however, that the substrate present in the tank and its characteristic properties are not sufficiently taken into account.

It is therefore the object of the present invention to provide a method for producing biogas with which to better take account of the properties of the substrate present in the digester.

SUMMARY

The method according to the invention produces biogas by means of at least one digester which is at least partially filled with a substrate. At least one agitating device controlled by a control device is disposed in the digester. According to the invention, at least the following process steps are provided in the sequence indicated or in another useful sequence:
a) a target load curve is lodged in the control device which is in particular characteristic of the substrate present in the digester, or the controller accesses a lodged target load curve;
b) the control device prescribes a target speed of rotation;
c) the control device operates the agitating device at an actual speed of rotation corresponding to the prescribed target speed of rotation;
d) the control device captures an actual measurement value which is characteristic of the torque of the agitating device prevailing at the actual speed of rotation;
e) the control device derives from the actual measurement value an actual characteristic value of the applied torque of the agitating device;
f) the control device compares the derived actual characteristic value against the target characteristic value of the substrate as it ensues from the target load curve at the prescribed target speed of rotation; and
g) the control device controls the agitating device in dependence on the result of comparison.

The method according to the invention has many advantages. The method according to the invention lodges in the control device, a target load curve for the currently employed substrate and for controlling operation of the agitating device in dependence on this target load curve. If the substrate properties deviate from the target curve at certain times, the control device controls operation of the agitating device for example so as to once again homogenize the substrate as desired.

Substrate in the sense of the present application is understood to mean a substrate of organic matter or a fermentation substrate respectively. Organic or anorganic additives may be admixed to the organic matter for boosting the desired reaction.

The process step a) is carried out at the beginning of the process or originally, and a target load curve for a substrate or a mixture is lodged, i.e. stored, in the control device or elsewhere. This process step may be carried out in operation on a regular basis or periodically, for example if the substrate or its composition changes.

The actual measurement value is characteristic of the torque at the actual speed of rotation. This means that a characteristic value of the current torque can be derived from the actual measurement value. An amount for the torque can for example be directly captured as a measurement value. Alternately, it is possible to employ as a measurement value for example the electric power required by the agitating device. The known physical formulas allow to conclude the torque from the electric power and the known actual speed of rotation. Any losses occurring may be computed and subtracted. Thus, for example the efficiency of an electric motor or a hydraulic motor and the efficiency of the transformation of a gear transmission is a constant quantity specific to a device and optionally power related.

These constant quantities or characteristics may be lodged in the control device so as to allow sufficiently precise conclusions about the actual torque, for example from the currently required, actual power of the agitating device.

In a preferred specific embodiment, the control device determines in a process step h) whether the actual characteristic value lies within a prescribed tolerance range around the target load curve at the target speed of rotation. This subdivides the result of comparison in three ranges, i.e. either the actual characteristic value lies beneath the target load curve and outside the prescribed tolerance range, or the actual characteristic value lies above the target load curve and outside the prescribed tolerance range, or the actual characteristic value lies within the prescribed tolerance range. It is insignificant whether an actual measurement value lies precisely on the target load curve or slightly off but within the prescribed tolerance range.

In all the specific embodiments, it is particularly preferred for the tolerance range to be dependent on the speed of rotation. It is also possible for the tolerance range to be dependent on the torque or on the current power. It is also possible for the tolerance range to define a constant quantity or a relative deviation from the target load curve. Preferably, the following process steps i1) through i4) are carried out in a loop, optionally repeatedly if the actual characteristic value lies beneath the target characteristic value and outside the tolerance range:
 i1) the actual speed of rotation of the agitating device is increased a predetermined amount;
 i2) a new actual measurement value at the new actual speed of rotation is captured;
 i3) a new actual characteristic value of the torque of the agitating device is derived from the new actual measurement value; and
 i4) the loop is exited when the derived new actual characteristic value lies within the prescribed tolerance range of the target load curve at the target speed of rotation.

In another preferred embodiment, the following process steps j1) through j4) are carried out accordingly in a loop if the actual characteristic value of the torque lies above the target characteristic value and outside the tolerance range:
 j1) the actual speed of rotation of the agitating device is decreased a predetermined amount;
 j2) a new actual measurement value at the new actual speed of rotation is captured;
 j3) a new actual characteristic value of the torque of the agitating device is derived from the new actual measurement value; and
 j4) the loop is exited when the derived new actual characteristic value lies within the prescribed tolerance range of the target load curve at the target speed of rotation.

Preferably, the extent of the tolerance range is dependent on the target characteristic value (torque) of the target load curve at the target speed of rotation. In simple and preferred configurations, the tolerance range defines a deviation percentage. In preferred configurations the tolerance range allows +/−33% deviation from the target characteristic value of the torque. In preferred configurations the tolerance range defines a deviation of up to +/−25% deviation from the target characteristic value. In specific embodiments the tolerance range may be limited to +/−20% or in particular also to +/−10% deviation or possibly also to +/−5% deviation from the target characteristic value. A still further limitation of the tolerance range is as a rule not provided. This avoids e.g. control fluctuations. The primary purpose is in particular not energy optimisation nor keeping the power input constant but optimising the agitating result. Likewise, readjustment of the power output is as a rule not intended but adjustment of desired operating points is so as to ensure optimal thorough mixing of the substrate.

The tolerance range is preferably dependent on the target speed of rotation but not on the actual speed of rotation. The tolerance range may be changed by percent or in steps via the speed of rotation.

In case that in any one step the target load curve and the tolerance range are completely exceeded, countercontrolling is feasible. Thus, if the actual characteristic value firstly lies above the target characteristic value and outside the tolerance range and after decreasing the actual speed of rotation it does not lie within the tolerance range by a predetermined amount but beneath the target load curve and outside the tolerance range, then the actual speed of rotation is increased in the next process step for example by half a predetermined amount. The reversed order of proceeding is possible in case that the actual characteristic value firstly lies beneath the target characteristic value and outside the tolerance range and after increasing the actual speed of rotation it lies above the target characteristic value and outside the tolerance range.

In particularly preferred specific embodiments, the actual speed of rotation is maintained as set for the remainder of an agitating cycle or for a predetermined time if the actual characteristic value lies within the prescribed tolerance range around the target load curve at the prescribed target speed of rotation. This allows the system time for homogenization. Too frequent control steps, which might lead to instabilities, are avoided.

Preferably, the agitating device is switched off or its power considerably reduced as an agitating cycle ends or after a predetermined time has passed. During a subsequent rest cycle, the agitating device remains switched off or continues operating at considerably reduced power. This saves considerable energy since the agitating device does not need to be continuously driven over the entire operating period. Periodic stirring is fully sufficient in most cases. For example, if an agitating cycle of 10 minutes or 1 hour and a corresponding rest period of 5 minutes, 10 minutes, 20 minutes, or half an hour or 1 hour or 2 hours is provided, the overall energy requirement may be reduced by 30%, 50% or more. For energy saving it is ultimately largely insignificant whether the agitating device for example continues operating at 10% power or it is stopped completely.

A rest cycle is preferably followed by a new agitating cycle. Particularly preferably an agitating cycle and a rest cycle alternate successively periodically.

When a new agitating cycle is started, the process steps b), c), d), e), f), g) and h) indicated above are preferably carried out. This means that the control device firstly prescribes a target speed of rotation and that subsequently the control device operates the agitating device at an actual speed of rotation corresponding to the prescribed target speed of rotation. The control device captures an actual measurement value which is characteristic of the torque of the agitating device at the actual speed of rotation. The control device derives from the actual measurement value an actual characteristic value of the applied torque of the agitating device. Furthermore, the control device controls the agitating device in dependence on the result of comparison. Finally, the control device determines whether the actual characteristic value lies within a prescribed tolerance range around the target load curve at the target speed of rotation.

There is no need to prescribe a new target load curve. It is possible, however, to adapt, or re-prescribe, the target load curve as required or periodically.

Preferably the process steps i1) through i4) indicated above and/or the process steps j1) through j4) are carried out, optionally repeatedly, in dependence on the results obtained. This means that the actual speed of rotation of the agitating device is increased a predetermined amount if the actual characteristic value lies beneath the target characteristic value and outside the tolerance range. Correspondingly the actual speed of rotation of the agitating device is decreased a predetermined amount if the actual characteristic value lies above the target characteristic value and outside the tolerance range. After increasing or decreasing the actual speed of rotation, a new actual measurement value is captured at the new actual speed of rotation from which a new actual characteristic value is derived. The loop runs until the actual characteristic value lies within the prescribed tolerance range around the target load curve or until the loop is exited, optionally after a predetermined quantity of loop runs.

The prescribed target speed of rotation is preferably dependent on the substrate and/or its composition and/or the desired biogas production.

Preferably, an actual speed of rotation is set in every agitating cycle in dependence on the target load curve. Setting the actual speed of rotation may be by iterative method until the actual speed of rotation lies within the prescribed tolerance range around the target load curve at the target speed of rotation. After setting the actual speed of rotation, the actual speed of rotation is maintained for the remainder of the agitating cycle. A first counter is incremented when the actual speed of rotation is higher than the prescribed target speed of rotation and/or a second counter is incremented when the actual speed of rotation is slower than the prescribed target speed of rotation. This achieves a simple amount for whether the target load curve is directly achieved every time, or whether the actual speed of rotation always requires modifications. Moreover, the quantity of changes is recorded so as to allow their evaluation.

Accordingly, it is preferred to modify the fed quantity of substrate and/or the composition of the fed substrate and/or the type and clock mode of operation of the agitating device and/or to feed additives when the first and/or second counter exceeds a prescribed threshold.

For example, too frequent deviations of the actual characteristic value from the target characteristic value may be attributed to a less than thorough mixing or an incorrect composition of the substrate.

The prescribed threshold in particular also depends on the number of agitating cycles. It is also possible and preferred to reset the first or second counter as the other of the counters is increased. An oscillation of the actual characteristic value around the target load curve from agitating cycle to agitating cycle then does not require any other action. Long-term evaluations may optionally be drawn up to improve the system overall.

In the case that immediately successive modifications to the first and/or second counter reach a predetermined number, the substrate quantity fed is preferably changed from outside and/or the composition of the fed substrate is modified and/or additives are added.

In all the configurations, it is preferred to use as the actual measurement value an amount measured for the electric power of the agitating device or for a torque of the agitating device. The actual measurement value used for the electric power may be the electric power of the entire agitator. The torque may be determined by employing an expansion measuring strip.

Preferably, the control device operates the agitating device in particular as required, at regular intervals, or e.g. with a restart after maintenance or e.g. after feeding a charge of substrate, at a plurality of different speeds of rotation, capturing an amount for the required power of the agitating device at the different speeds of rotation to determine a characteristic load curve of the substrate.

The proceeding has many advantages. This process determines and stores a characteristic load curve of a substrate. This load curve may be used as the target load curve in the aforementioned process. This is very advantageous since a new target load curve can be determined and stored basically any time. It is not required to perform theoretical calculations and empirical or semi-empirical considerations of influences of a plurality of parameters and different substances but one can simply use the substrate charged at the time and the load curve ensuing therefrom may be prescribed as the target load curve for the further operation. This automatically takes account of e.g. regional differences in the composition and characteristics of organic matter. Moreover, the current composition of the substrate is used for a basis.

This allows the manufacturer or operator to determine a new target load curve basically anytime.

Preferably, the operation of the agitating device and/or the feeding of ferments and/or additives are modified in dependence on the determined characteristic load curve.

In preferred specific embodiments, the determined characteristic load curve is compared against a target load curve. In this operating mode a comparison of the determined characteristic load curve against a target load curve allows conclusions about the properties of the substrate present and its distribution within the digester. For example, if the load curve is captured in an upper region of the digester, a floating sludge layer may be concluded. If the load curve is captured in a lower region of the digester, then the lower area of the substrate is characterized by the determined load curve.

It is preferred to determine the characteristic load curve of the substrate periodically. A time interval between determining two characteristic load curves may be variable. It is also possible to provide a constant time interval between determining two load curves. It is in particular also possible and preferred to provide the time intervals between determining two characteristic load curves dependent on the result of a comparison of the characteristic load curve against a target load curve respectively substrate load curve.

The agitating device is particularly preferably displaced in height to determine a characteristic load curve of the substrate at least at two height positions. This allows to reliably detect inhomogeneities across the height of the digester.

Thus, the determined characteristic load curves allow conclusions about at least one substrate property at least at two different heights. For example, the result may show that mixture separation has occurred and stirring needs to be increased or intensified.

Accordingly, stirring is preferably provided in dependence on the determined characteristic load curves at least at two different heights for controlled influence on the substrate and in particular for local homogenization or modified distribution of substrate portions.

Controlled gas expulsion is possible and preferred wherein substrate flow through the agitating devices is substantially set in a helical pattern. Expulsion is preferred from bottom to top.

BRIEF DESCRIPTION OF THE DRAWINGS

Further advantages and applications of the present invention can be taken from the exemplary embodiment which will be described below with reference to the enclosed figures.

The figures show in:

FIG. 5 a sectional view of the drive motor of the agitating device according to FIG. 4;

FIG. 6 front view of the agitating device according to FIG. 5;

FIG. 6a an enlarged cross-sectional detail from FIG. 6;

DETAILED DESCRIPTION

Figure 1:
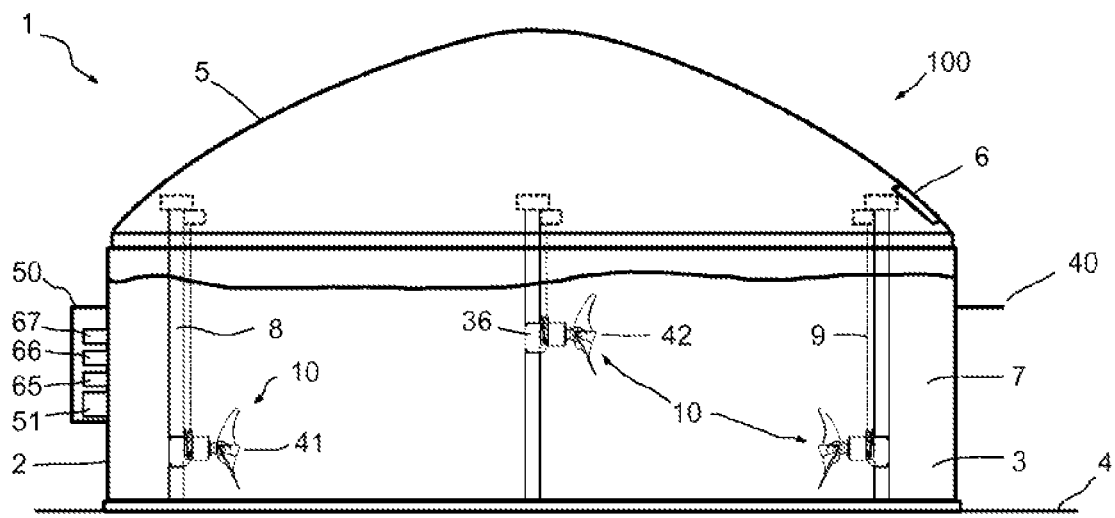
FIG. 1 a schematic lateral cross-section of a digester.

Referring to the figures an exemplary embodiment will now be discussed. FIG. 1 shows a simplistic side view of a digester 1 of a biogas plant 100.

The digester 1 is preferably approximately circular in cross section and is presently provided with a circumferential digester wall 2 for example of concrete or steel. The digester roof 5 may be configured as a flat steel or concrete roof, as may the floor. This digester roof 5 is formed by an in particular flexible material, extending upwardly from the wall so that a domed structure of the tank roof 5 is obtained. The inclination angle of the digester roof 5 depends on the specific conditions and may be 15 degrees or more and in particular 30 degrees or 45 degrees or more. Preferably the digester roof 5 is at least partially and in particular entirely removable to render the digester interior 3 accessible. In the digester interior 3 a substrate 7 is provided when in operation.

The digester roof 5 may be provided with at least one servicing opening 6 for example for servicing an agitator 10 disposed in the digester interior 3. A platform 40 may be attached for example to the outside of the digester wall 2 for an operator to stand on.

Figure 2:
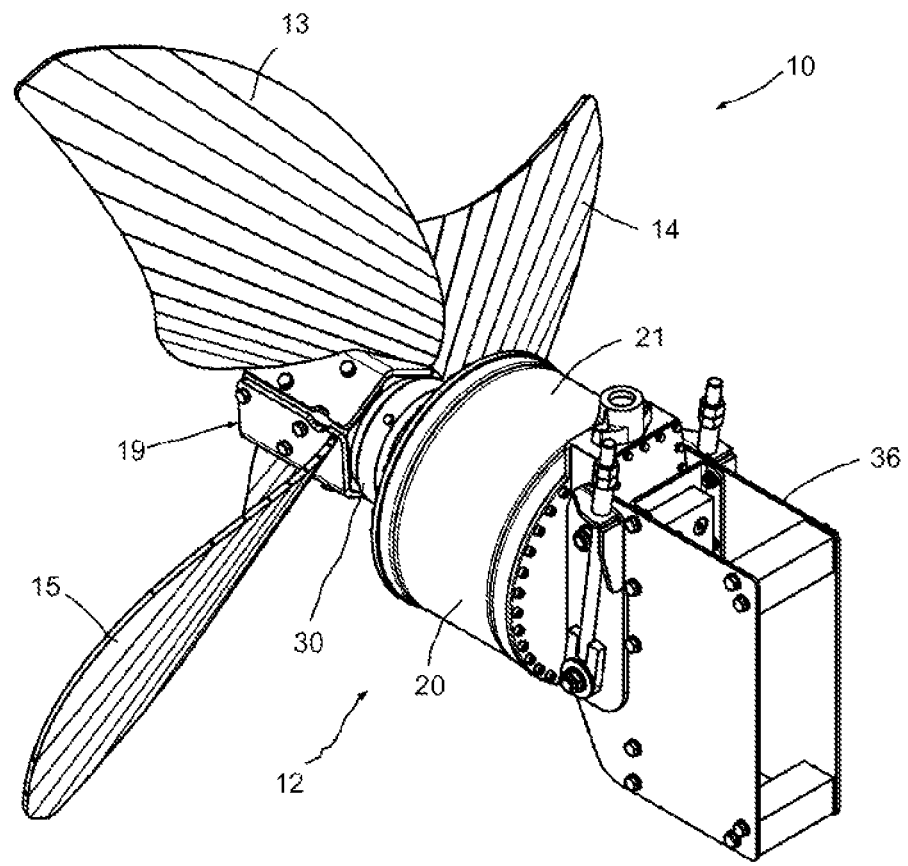
FIG. 2 a perspective view of an agitating device for the digester according to FIG. 1.

FIG. 2 shows a schematic perspective illustration of the agitating device 10 with the driving device 12. The agitating device 10 is received height-adjustable on the support unit 8 configured as a support rod by means of a console 36. The agitator 10 is pivotable together with the support unit 8 and may be rotated 360 degrees. This allows to swivel the agitator blades 13, 14 and 15 toward the digester wall 2 and to displace it upwardly for maintenance purposes where the agitating device is then accessible through the servicing opening 6.

As is shown in the FIG. 1, two, three or even more agitating devices 10 may be disposed in the digester interior 3 to thus ensure a reliable and sufficiently thorough mixing of the substrate 7. It is possible to position the various agitating devices 10 at different heights 41, 42, for agitating for example in the lower region of the digester 1 at the height position 41 while an upper region is mixed at the height position 42 so as to disintegrate or avoid floating sludge layers.

Other than the height positions 41 and 42 shown, other height positions are possible, in particular a mid-height position between the first height position 41 and the second height position 42.

Preferably at least two agitating devices 10 are provided each being pivotable around the axis of the support unit 8 so as to generate different degrees of thorough mixing and flow directions within the substrate 7. These agitating devices 10 may be oriented in the same direction of circulation or at an angle to one another or in opposite directions of circulation. They can be used at the same height or in different height positions. Each agitating device 10 is controlled either by its own control device 50 or by a control device 50 shared between the agitators respectively agitating devices 10. A frequency converter 51 is provided for selecting.

As is shown in FIG. 2, an agitating device in this exemplary embodiment shows three agitator blades 13, 14 and 15 which are attached to a blade hub 19. The blade hub 19 in turn is non-rotatably fixed to the drive shaft which is not visible in FIG. 2.

The driving device 12 comprises the drive motor 20 and the attachment device 30 which is fixed to the drive motor 20 housing. The drive motor 20 shows a large diameter which is substantially defined by the external diameter of the stator 21. The stator 21 with its outside surface forms part of the housing of the drive motor 20.

Figure 3:
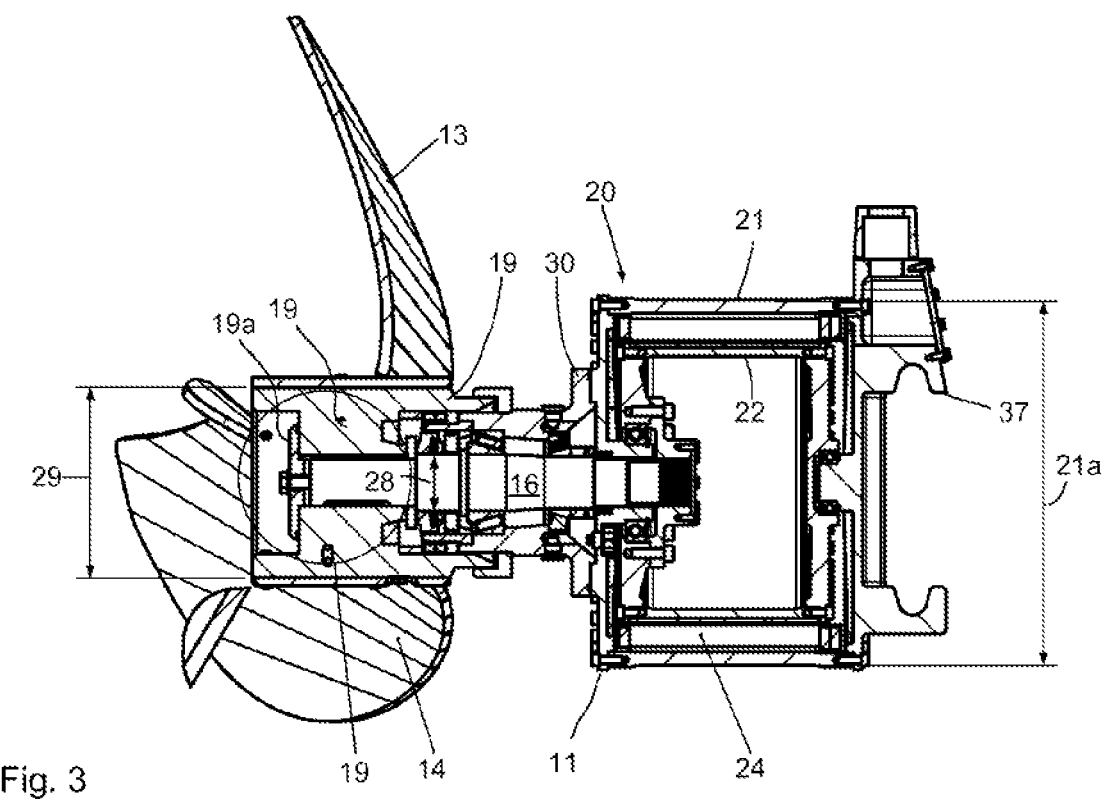
FIG. 3 a sectional schematic side view of the agitating device according to FIG. 2.

FIG. 3 shows a sectional schematic side view of the agitating device 10 with the rear agitator blades 13 and 14 visible.

It can be seen that an attachment device 30 is attached to the drive motor 20. The attachment device serves to support and guide the drive shaft 16. The blade hub 19 is attached to the drive shaft 16 to which the agitator blades 13 to 15 are in turn attached. The console accommodation 37 serves for fastening to the console 36. Part of the housing 11 is formed by the stator 21 which shows an external diameter 21a. A hollow rotor 22 is disposed in the interior of the stator 21. The stator 21 shows an external diameter 21a. The drive shaft 16 shows an external diameter 28. The external diameter 21a of the stator is multiple times larger than the external diameter 28 of the drive shaft 16. This achieves a particularly high rotational force of the drive motor 20. Also, an external diameter 29 of the blade hub 19 is considerably smaller than an external diameter 21a of the stator.

Figure 4:
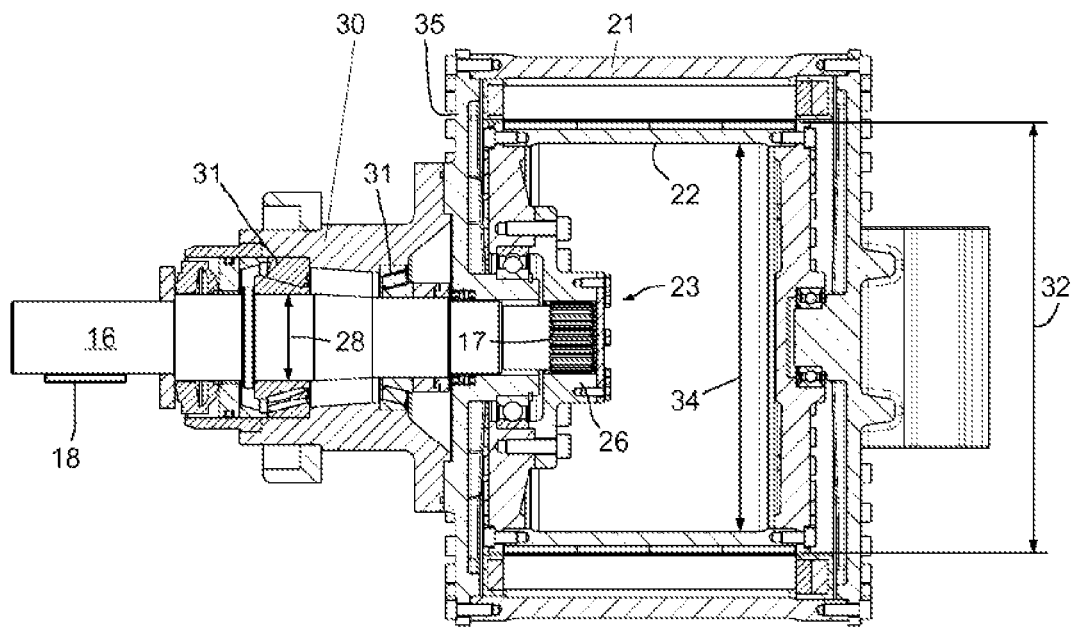
FIG. 4 a sectional schematic side view of the agitating device according to FIG. 3 without the agitator blades.

FIG. 4 shows in more detail a cross-section of the drive motor 20 with the attachment device 30 attached thereto. The attachment device 30 is fastened to the end cover 35 of the housing 11 of the drive motor 20. The interior of the attachment device 30 is provided with bearing devices 31 for supporting the drive shaft 16. The drive shaft 16 is provided with an engaging dog 18 which protrudes radially outwardly and enters into a corresponding groove or the like in the blade hub.

The drive shaft 16 is coupled with the rotor 22 via a coupling device 23 which in this instance is configured as a tooth flange 26 and seals the rotor 22 outwardly. The tooth flange 26 shows an internal toothing 27 which when mounted as shown in FIG. 4 is in engagement with the external toothing 17 of the drive shaft 16. The attachment device enables easy and ready mounting and simple exchange. If required, the attachment device together with the drive shaft is removed from the driving device 12 and may be exchanged for a new one.

In FIG. 4 the internal diameter 32 of the rotor 22 21 is shown. The external diameter 34 of the rotor 22 corresponds to the internal diameter of the stator 21.

The internal diameter 32 is a multiple of the external diameter 28 of the drive shaft 16 so that the drive motor 20 can transmit high rotational forces.

FIG. 5 shows the drive motor of the agitating device absent an attachment device in a section. The back face shows the console accommodation 37 and the front face shows the end cover 35. A shaft opening 38 is provided in the end cover 35 to receive the drive shaft 16. The shaft opening 38 is provided with at least one shaft seal 39 to seal the drive motor toward the interior.

When the drive shaft 16 is inserted into the shaft opening 38, the external toothing 17 of the drive shaft 16 engages the internal toothing 27 of the tooth flange 26 of the coupling device 23. There is non-rotatable coupling between the drive shaft and the drive motor 20. The architecture showing a hollow rotor 22 having a large internal diameter 32 enables a lightweight structure for transmitting high rotational forces. Moreover, exchanging the drive shaft 16 does not require to open the drive motor 20.

FIGS. 6 and 6a show a front view respectively an enlarged, sectional front view of the drive motor 20 without the attachment device 30. The console accommodation 37 can be seen in the background while at the front the end cover 35 with the shaft opening 38 provided therein can be seen. One can see the tooth flange 26 with the internal toothing 27.

FIG. 6*a* shows an enlarged sectional view of a detail of the drive motor 20 showing a triangle segment of the stator 21 and the rotor 22. The stator 21 is provided with a number of windings 24 while permanent magnets 25 are disposed on the rotor 22. The number of windings is preferably larger than the number of permanent magnets and particularly preferably the permanent magnets and windings are more than 30 and particularly preferably more than 50 in number. The high number of windings and permanent magnets enable precise controlling, and high rotational force is enabled. In preferred configurations the drive motor 20 is configured as a torque motor. A preferred configuration e.g. provides for a minimum of 70 poles, 35 pole pairs and/or 280 magnets.

Figure 7:
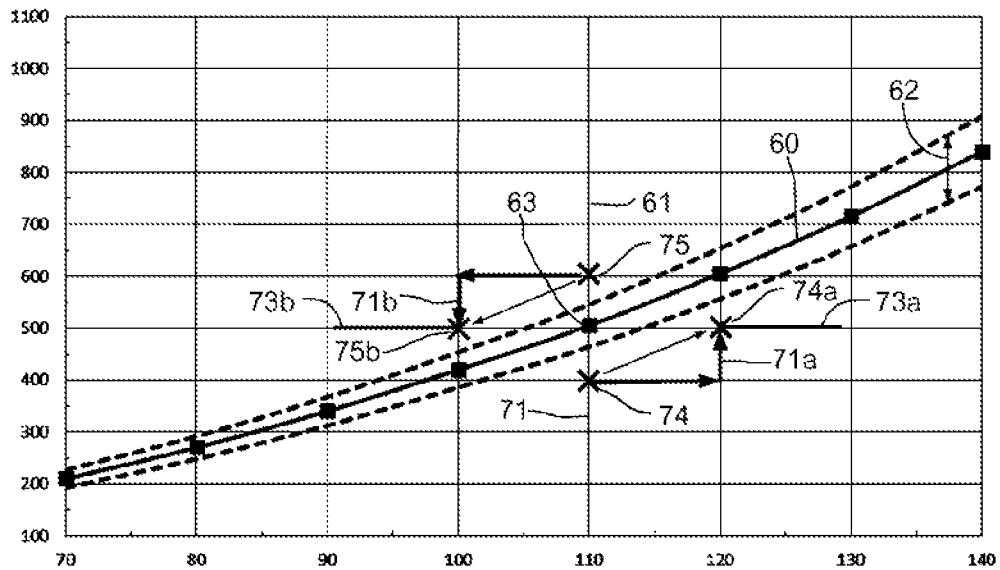
FIG. 7 a target load curve for a given substrate.

FIG. 7 shows a target load curve 60 for a given substrate 7 and a tolerance range 62 showing a percentage extension around the target load curve 60. The tolerance range 62 may show a fixed value extension around the target load curve. A relative percentage of for example 5% or 10% deviation upwardly and downwardly is also possible.

In FIG. 7 the rotational force is plotted in Newton metres over the speed of rotation in revolutions per minute for a concrete case. This target load curve may be determined empirically and may apply for example to a specific substrate having a specific composition etc. This target load curve 60 is prescribed to enable specific control of the agitating device 10 respectively the agitating devices 10 via the control device 50.

As can be seen, the rotational force increases with increasing speed of rotation.

Controlling the digester 1 basically works in that at the start of the plant, a target load curve 60 is first prescribed or retrieved from a memory device. Thereafter the control device 50 prescribes a target speed of rotation 61. The control device 50 operates the agitating device 10 at an actual speed of rotation that corresponds at least roughly to the prescribed target speed of rotation. As the actual speed of rotation 71 is reached, an actual measurement value is captured at the operating point 74, 75 which value is characteristic of the torque or of the power of the agitating device 10 at the actual speed of rotation 71. For example, an expansion measuring strip or the like on the drive shaft or in or at the rotor may serve to capture a measurement value that is characteristic of the rotational force applied. Or else it is possible and preferred to derive such measurement value 73*a*, 73*b* directly from the electric power consumption of the agitating device 10. The measurement value can be directly used as a characteristic value or the characteristic value is computed from the measurement value.

An actual characteristic value 74, 75 is derived from the measurement value. This actual characteristic value is compared against the target characteristic value 63 for the substrate ensuing from the target load curve 60 at the prescribed target speed of rotation 61.

If the control device determines that the rotational force occurring at the actual speed of rotation 71 lies outside the tolerance range 62 at the target speed of rotation 61, then either the actual speed of rotation is increased or else decreased a predetermined amount, depending on whether the actual rotational force is above or beneath the target characteristic value 63.

In the exemplary embodiment shown the actual speed of rotation 71 is increased or reduced in steps of 10 revolutions/min. It is also possible for the speed of rotation to be modified in smaller steps or else by percentage in dependence on the target speed of rotation 61.

After increasing the actual speed of rotation to the value 71*a* the actual measurement value and thus the actual characteristic value increases to the value 73*a* which in the presently selected exemplary embodiment lies within the tolerance range 62 around the target load curve 60 at the target speed of rotation 61. Due to the increase of the speed of rotation the rotational force has increased far enough for the rotational force to now lie in the desired range.

In the reversed case, i.e. if at the target speed of rotation 61 a rotational force is applied that lies above the tolerance range 62 of the target load curve 60, then the actual speed of rotation 71 is reduced to the actual speed of rotation 71*b*. Due to the lower speed of rotation the rotational force required also decreases so that the actual characteristic value 73*b* now, at the decreased actual speed of rotation 71*b*, lies within the tolerance range 62 of the target load curve 60 at the target speed of rotation 61.

Thus, in both cases—i.e. given a rotational force exceeding upwardly and downwardly—the actual rotational force is safely limited to within the desired range. Thereafter the remaining agitating cycle continues in the agitating device at the thus determined actual speed of rotation 71, 71*a*, or 71*b*.

In case that the increase or decrease of the actual rotational force in one step is not sufficient, the afore described loop is run iteratively until the actual rotational force lies in the desired target range.

This means that in the process flow a target load curve 60 is firstly lodged in the control device 50 or a target load curve 60 is retrieved from a memory device or from the control device 50 respectively.

The control device 50 prescribes a target speed of rotation as each agitating cycle begins, firstly the target speed of rotation 61. The control device 50 controls the agitating device 10 accordingly so that the agitating device 10 reaches an actual speed of rotation 71 corresponding to the prescribed target speed of rotation 61 in the scope of control accuracy. This results—depending on the substrate properties—in an operating point 74 or an operating point 75.

Thereafter the control device captures an actual measurement value 81 (see FIG. 8), which is characteristic of the torque of the agitating device 10 at the actual speed of rotation 71. The measurement value 81 is in particular the electric power consumption of the agitating device at the actual speed of rotation 71, although it may directly be the rotational force.

The control device 50 derives from the actual measurement value, taking into account the equipment factors, the losses occurring etc., an actual characteristic value of the rotational force applied. Or else the actual characteristic value may correspond to the power output at the actual speed of rotation since the rotational force can be computed from the output if the speed of rotation is known. In simple cases the actual characteristic value may correspond to the actual measurement value.

Thereafter the control device 50 compares the derived actual characteristic value 81 against the target characteristic value 63 resulting from the target load curve 60 at the prescribed target speed of rotation 61.

The control device 50 controls the agitating device 10 in dependence on the result of comparison.

The control device 50 determines in particular whether the actual characteristic value lies within a prescribed tolerance range 62 around the target load curve 60 at the target speed of rotation 61.

Thereafter, in the case of the operating point 74, namely if the actual characteristic value lies beneath the target characteristic value 63 and outside the tolerance range 62, the actual speed of rotation 71 of the agitating device 10 is increased a predetermined amount (presently, 10 revolutions/min) and a new operating point 74a ensues at the new actual speed of rotation 71a showing an actual rotational force 73a respectively a new actual characteristic value 73a.

Then the new operating point 74a lies within the prescribed tolerance range 62 of the target load curve 60 at the target speed of rotation 61 and the agitating cycle continues at this speed of rotation.

In the case of the operating point 75, namely if the pertaining actual characteristic value lies above the target characteristic value 63 and outside the tolerance range 62, then the actual speed of rotation 71 of the agitating device 10 is decreased a predetermined amount (presently, 10 revolutions/min) and a new operating point 75b ensues at the new actual speed of rotation 71b showing an actual rotational force 73b respectively a new actual characteristic value 73b.

Now the new operating point 75a also lies within the prescribed tolerance range 62 of the target load curve 60 at the target speed of rotation 61 and the agitating cycle continues at this speed of rotation 71b.

Figure 8:
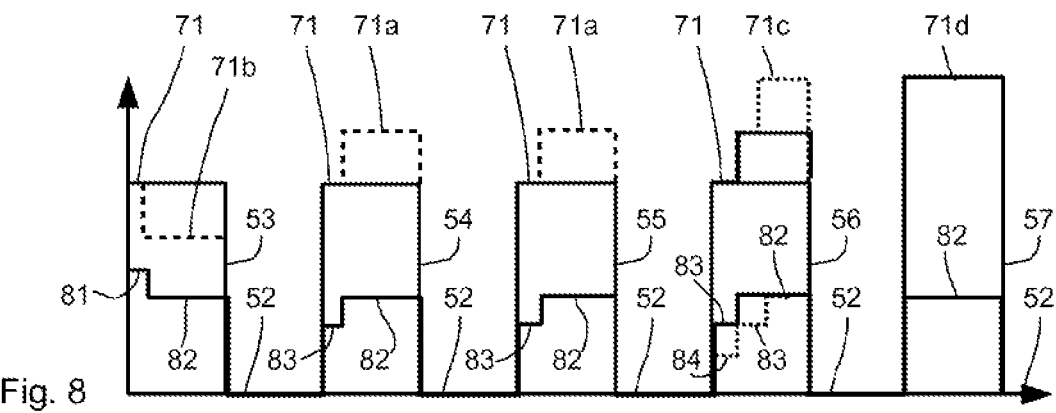
FIG. 8 the speed of rotation of the agitating device over time.

FIG. 8 shows a schematic time control curve for illustrating this principle. The speeds of rotation 71, 71a, 71b, 71c and 71d of the agitating device 10, the measurement values 81 to 84 and the characteristic values or rotational forces 91 to 94 over time resulting from the electric power consumption are plotted. A number of agitating cycles 53 to 57 interrupted by agitating stops 52 are illustrated.

At the beginning of the agitating cycle 53 the agitating device 10 is firstly controlled or operated at an actual speed of rotation 71 corresponding to the target speed of rotation 61. Since the measured electric output 81 respectively the resulting rotational force 91 and thus the characteristic value firstly lies above the desired target characteristic value, the actual speed of rotation is decreased to the value 71b so that the electric power consumption 82 decreases, resulting in a suitable torque respectively characteristic value 92 which now lies within the desired range. Then this speed of rotation 71b is maintained until the agitating cycle 53 ends.

The characteristic value 91 and the measurement value 81 (e.g. the power) may be linked linearly or by way of another formula. It is also possible to directly use the measurement values 81 to 84 for the characteristic values 91 to 94 if an unambiguous and reproducible association is given.

The agitating cycle 53 is followed by a rest cycle 52 in which the speed of rotation of the agitating device 10 is decreased to zero.

The following agitating cycle 54 then starts again at the actual speed of rotation 71 which corresponds to the target speed of rotation 61. In the agitating cycle 54 the electric power consumption 83 and thus the characteristic value respectively the torque 93 is firstly beneath the target value so that the speed of rotation is increased to the actual speed of rotation 71a. Thereafter the power consumption 82 and the rotational force 92 respectively the actual characteristic value 92 lie in the desired range. In the shown example the rotational force is computed from the power consumption with the speed of rotation.

The next rest cycle is followed by an agitating cycle 55 which in turn starts at the actual speed of rotation 71 which corresponds to the target speed of rotation 61. In this agitating cycle the power consumption 83 and thus the rotational force 93 detected is again too low so that the speed of rotation is increased to the actual speed of rotation 71a at which the desired actual rotational force 92 is applied.

In the next agitating cycle 56 the behaviour may be identical as is illustrated by the unbroken line. Or else it is possible that the properties of the substrate 7 have changed and a further increase of the actual speed of rotation to a still higher value 71c is required as is illustrated by the broken line. The variant shown in the broken line in the agitating cycle 56 requires an increase of the actual speed of rotation to the values 71a and 71c in two steps until the desired rotational force is obtained. Firstly, the measurement value 84 and the pertaining characteristic value 94 are too low, then they increase to the measurement value 83 respectively the characteristic value 93 and only as the speed of rotation is increased to the value 71d do they reach the measurement value 82 and the desired rotational force respectively the characteristic value 92.

Every time the actual speed of rotation needs to be increased in successive agitating cycles a first counter 65 (see FIG. 1) is increased so that in the fourth agitating cycle 56 the counter shows the value 3. As a prescribed threshold 67 of e.g. 3, 5 or 10 or the like is exceeded, a new start value for the target speed of rotation is prescribed in the agitating cycle 57 following next. The new target value is then directly higher than the preceding value. This is exemplarily illustrated in FIG. 8 in the last agitating cycle in which an actual speed of rotation 71d is set.

If reversely the actual speed of rotation is decreased, a second counter 66 is increased. If it exceeds a threshold 67 (the same or different), there will be a suitable response.

If the first counter 65 or the second counter 66 exceeds a threshold 67 since displacements in the same direction had been required in successive agitating cycles, in particular instructions for action are issued such as feed more or less (depending on the direction), or another agitator position is selected, or longer (or shorter) agitating cycles are performed.

Figure 9:
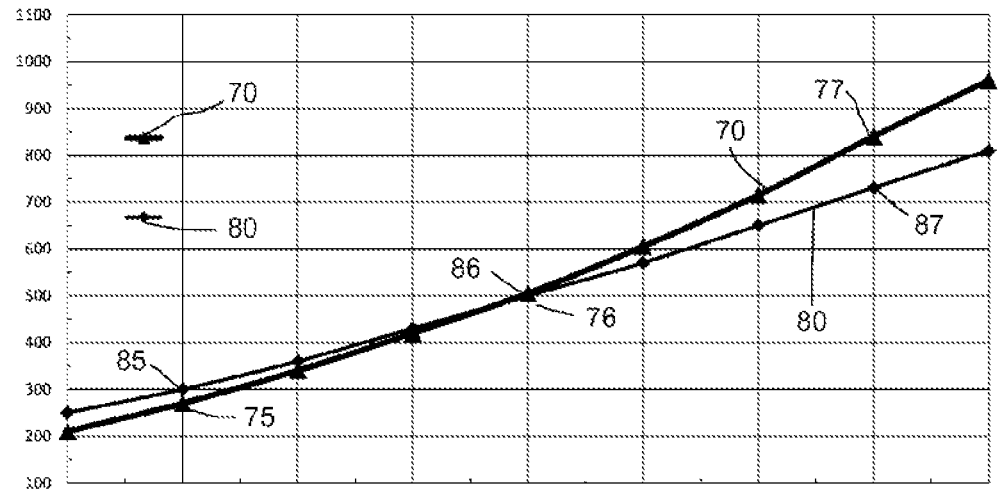
FIG. 9 an illustration of two different, captured load curves.

FIG. 9 shows two different load curves 70 and 80, with the rotational force plotted in Newton metres (Nm) over the speed of rotation in revolutions per minute.

The load curves 70 and 80 represent two different substrates 7 showing the load curve 70 for the material "liquid pig manure" and representing a low-viscosity medium. The load curve 80 was captured using the medium fermentation residue of a digester. This substrate for the curve 80 represents medium-viscosity matter.

In this exemplary embodiment the two load curves 70 and 80 intersect at the measuring points 76 and 86 while in the measuring point 75 the required rotational force of the load curve 70 is lower than the respective rotational force in the measuring point 85 of the load curve 80.

While in this exemplary embodiment, given the illustrated load curves 70 and 80, the rotational force required for rotation is firstly higher in the load curve 80 at low speeds of rotation (measuring points 75, 85), the rotational force required for rotating the agitating device 10 at higher speeds of rotation decreases in the load curve 80 relative to the load curve 70.

This means that the digester 1 and the agitating device 10 disposed therein allow to take up load curves 70, 80 of the substrate 7 present therein. The torque path of the load curves 70 or 80 allows to draw conclusions about the prevailing properties and optionally the composition of the substrate 7 concerned.

For example, the load curve 70 may represent the target load curve for the substrate 7 used. Now if during operation a load curve with the agitating device and the control device 50 is recorded and the recorded load curve corresponds to the load curve 80, then the differences between the load curves 70 and 80 may be evaluated and concrete recommendations for action can be issued or directly initiated for adapting the load curve present in the substrate to the target load curve. For example, the composition of the matter supplied may be changed. It is also possible to change the operating conditions of the agitating devices and for example to increase, or optionally decrease, the intensity of agitating for a specific time period. It is also possible to change the gas offtake in dependence on the captured load curves.

It is also possible and preferred to control the agitating device 10 in dependence on the desired gas offtake. For example, higher sums of money for delivered power may be paid during specific times so as to provide an incentive to produce more gas and in particular electric power during these times. Thus, selective use of the agitating devices may take care that at, or prior to (for storage), those times, gas output is increased.

The agitating devices which are disposed for automatic displacement along the height of the support units 8 also allow to take up load curves 70, 80 of the substrate 7 located in the digester interior at different height positions 41, 42 etc. Different load curves 70, 80 at different heights allow conclusions about the presence and size of floating sludge layers and further parameters of the substrate. For example, if low viscosity is detected at certain height layers, this may be indicative of certain components floating upwardly or other components settling down. Suitable measurements in layers above and below thus allow conclusions of an inhomogeneous distribution in the substrate in the digester.

Suitable controlling of the agitating devices 10 (height, angle, intensity) may achieve more complete thorough mixing.

Controlled strategies for expelling gas are possible, such as a helical automatic arrangement where expelling takes place from bottom to top.

The recording of load curves 70, 80 also allows to replace at any time the target load curve lodged in the control device 50 by a currently captured load curve. When the operator or the manufacturer finds that the digester 1 behaves as desired in the present operation, a new target load curve 60 may be created and stored. This may be provided on a regular basis or only as required, for example as the composition of the supplied substrate changes.

On the whole the invention provides an agitator technology dependent on the medium where automatic control is provided in dependence on the currently prevailing conditions of the substrate.

Operation is carried out so as to be energy saving. Controlling homogenizes the substrate. The target values ensue from the medium employed. The state of the medium is captured locally.

The measurement and control values allow to issue measures for action. Deviations are captured and corrective measures are carried out or suggested. In case of incidents, measures for action are suggested. On the whole, complete monitoring and remote system diagnostics are possible. Servicing may be provided on site.

The agitator used is a highly efficient, gearless agitator having a low-loss direct drive ensuring a speed of up to 1000 Nm that is constant over the speed of rotation. The speed range of rotation is continuous, extending from 0-250 revolutions per minute.

The output range in the device described in the exemplary embodiment is 4 to 12.5 kW. The volume flow is up to 153 m3/min. The comfortable height adjusting and swivelling device achieves safe positioning as to height and angles.

Controlling may be done by means of a multifunction control of the process data such as volume flow, pressure, torque, power, SET parameter curve, parameter curve function.

While a particular embodiment of the method for operating a stirring device and a fermenter has been shown and described, it will be appreciated by those skilled in the art that changes and modifications may be made thereto without departing from the invention in its broader aspects and as set forth in the following claims.

LIST OF REFERENCE NUMERALS

1 digester
2 digester wall
3 digester interior
4 horizontal
5 digester roof
6 servicing opening
7 substrate
8 support unit
9 cable
10 agitating device, agitator
11 housing
12 driving device
13-15 agitator blade
16 drive shaft
17 external toothing
18 engaging dog
19 blade hub
19a fixing unit
20 drive motor
21 stator external diameter 21
22 rotor
23 coupling device
24 winding
25 permanent magnet
26 tooth flange
27 internal toothing 26
28 external diameter 16
29 external diameter 19
30 attachment device
31 bearing device 30
32 internal diameter 22
33 hollow portion of 22
34 external diameter 22
35 end cover
36 console
37 console accommodation
38 shaft opening
39 shaft seal
40 platform
41 1st height position
42 2nd height position
50 control device
51 frequency converter
52 rest cycle
53-57 agitating cycle 60 target load curve
61 target speed of rotation
62 tolerance range
63 target characteristic value
65 first counter
66 second counter
67 threshold 21a
70 load curve
71 actual speed of rotation
71a, 71b actual speed of rotation
72a, 72b actual measurement value
73a, 73b actual characteristic value
74, 74a operating point
75, 75a operating point
81-84 measurement value
91-94 characteristic value
100 biogas plant

What is claimed is:

1. A method for automatically operating a digester which is at least partially filled with a substrate, the method comprising:
   a control device operating an agitating device at a plurality of different speeds of rotation at a first height position in the digester, and capturing an amount for a required power of the agitating device at the plurality of different speeds of rotation to determine a first characteristic load curve of the substrate;
   the control device displacing the agitating device in height to a second height position in the digester;
   the control device operating the agitating device at a plurality of different speeds of rotation at the second height position in the digester, and capturing an amount for a required power of the agitating device at the plurality of different speeds of rotation to determine a second characteristic load curve of the substrate;
   performing at the first and the second height position an agitating cycle, respectively, each comprising:
      prescribing, by the control device, a target speed of rotation;
      operating, by the control device, the agitating device at an actual speed of rotation corresponding to the target speed of rotation;
      capturing, by the control device, an actual measurement value which is characteristic of a torque of the agitating device at the actual speed of rotation;
      deriving, by the control device, from the actual measurement value an actual characteristic value of an applied torque of the agitating device;
      comparing, by the control device, the actual characteristic value derived at the first height position against a target characteristic value of the substrate resulting from the first characteristic load curve at the target speed of rotation and the actual characteristic value derived at the second height position against a target characteristic value of the substrate resulting from the second characteristic load curve at the target speed of rotation; and
      controlling, by the control device, the agitating device based on results of comparison.

2. The method according to claim 1, further comprising determining, by the control device, whether the actual characteristic values derived at the first and the second height position lie within a prescribed tolerance range around the first and the second characteristic load curve, respectively, at the target speed of rotation.

3. The method according to claim 2, wherein in response to determining that the actual characteristic values of the first and the second height position lie beneath the target characteristic values and outside the prescribed tolerance range of the first and the second height position, respectively, the method further comprises the following performed in a loop:
   increasing the actual speed of rotation of the agitating device a predetermined amount to a new actual speed of rotation;
   capturing a new actual measurement value at the new actual speed of rotation;
   deriving a new actual characteristic value from the new actual measurement value; and
   exiting the loop in response to determined that the new actual characteristic value lies within the prescribed tolerance range of the first and the second characteristic load curves at the target speed of rotation.

4. The method according to claim 2, wherein in response to determining that the actual characteristic values of the first and the second height position lie above the target characteristic value and outside the prescribed tolerance range of the first and the second height position, respectively, the method further comprises the following performed in a loop:
   decreasing the actual speed of rotation of the agitating device a predetermined amount to a new actual speed of rotation;
   capturing a new actual measurement value at the new actual speed of rotation;
   deriving a new actual characteristic value from the new actual measurement value; and
   exiting the loop exited in response to determining that the new actual characteristic value lies within the prescribed tolerance range of the first and the second characteristic load curve at the target speed of rotation.

5. The method according to claim 2, wherein the actual speed of rotation is maintained as set for a remainder of the agitating cycle in response to determining that the actual characteristic values of the first and the second height position lie within the prescribed tolerance range around the first and the second characteristic load curves, respectively, at the target speed of rotation.

6. The method according to claim 1, wherein the agitating device is switched off as the agitating cycle ends.

7. The method according to claim 6, wherein the rest cycle is followed by a new agitating cycle.

8. The method according to claim 2, further comprising performing a new agitating cycle.

9. The method according to claim 1, wherein the target speed of rotation is dependent on at least one of the substrate and a composition of the substrate and a predetermined biogas production.

10. The method according to claim 1, wherein the actual speed of rotation is set in every agitating cycle based on the first and the second characteristic load curve and maintained thereafter for a remainder of the agitating cycle;
    and wherein a first counter is incremented in response to determining that the actual speed of rotation is higher than the target speed of rotation;
    and wherein a second counter is incremented when the actual speed of rotation is slower than the target speed of rotation.

11. The method according to claim 10, further comprising modifying at least one of a quantity of substrate fed into the digester, and changing a composition of the substrate-fed into the digester, and supplying additives in response to determining that at least one of the first and the second counter exceeds a prescribed threshold.

12. The method according to claim 11, wherein the prescribed threshold also depends on the number of agitating cycles.

13. The method according to claim 1, wherein the actual measurement value used is an amount measured for a torque of the agitating device.

14. The method according to claim 1, further comprising:
storing the first and the second characteristic load curve in the control device;
performing at the first and the second height position an agitating cycle, respectively, each comprising:
prescribing, by the control device, a target speed of rotation, wherein the target speed of rotation is dependent on the substrate;
operating, by the control device, the agitating device at an actual speed of rotation corresponding to the target speed of rotation;
capturing, by the control device, an actual measurement value which is characteristic of a torque of the agitating device at the actual speed of rotation;
deriving, by the control device, from the actual measurement value an actual characteristic value of an applied torque of the agitating device;
comparing, by the control device, the actual characteristic value derived at the first height position against a target characteristic value of the substrate resulting from the first characteristic load curve at the target speed of rotation and the actual characteristic value derived at the second height position against a target characteristic value of the substrate resulting from the second characteristic load curve at the target speed of rotation;
controlling, by the control device, the agitating device based on results of comparison.

15. The method according to claim 14, wherein after storing the first and the second characteristic load curve the method further comprises:
feeding of ferments; and
agitating, by the agitating device, the substrate at the first and second height positions based on the first and second characteristic load curves for locally homogenizing the substrate.

* * * * *